(12) United States Patent
Steinhilber et al.

(10) Patent No.: US 7,135,452 B1
(45) Date of Patent: Nov. 14, 2006

(54) RECOMBINANT SP-A FOR THE TREATMENT OR PREVENTION OF PULMONARY INFECTION AND INFLAMMATION

(75) Inventors: Wolfram Steinhilber, Stockach (DE); Jeffrey A. Whitsett, Cincinnati, OH (US); Ann Marie Levine, Cincinnati, OH (US); Thomas R. Korfhagen, Cincinnati, OH (US)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 09/889,348

(22) PCT Filed: Jan. 18, 2000

(86) PCT No.: PCT/EP00/00324

§ 371 (c)(1),
(2), (4) Date: Sep. 26, 2001

(87) PCT Pub. No.: WO00/43026

PCT Pub. Date: Jul. 27, 2000

Related U.S. Application Data

(60) Provisional application No. 60/155,268, filed on Jan. 19, 1999.

(51) Int. Cl.
*A61K 38/00* (2006.01)
*C12N 15/00* (2006.01)

(52) U.S. Cl. ............. 514/2; 435/69.1; 514/12; 514/885

(58) Field of Classification Search ............ 435/69.1; 514/2, 12, 885
See application file for complete search history.

(56) References Cited

U.S. PATENT DOCUMENTS 5,840,527 A  11/1998  Schilling, Jr. et al. ..... 435/69.1
6,267,958 B1 *  7/2001  Andya et al. ............ 424/130.1

FOREIGN PATENT DOCUMENTS

EP          0 652 011        5/1995

OTHER PUBLICATIONS

Borron et al. Surfactant protein A inhibits T cell proliferation via its collagen-like tail and a 210-kDa receptor. Oct. 1998, Am. J. Physiol. vol. 275 (Lung Cell. Mol. Physiol. 19) pp. L679-L686.*
McCormack et al. The Structure and Function of Surfactant Protein A. 1994, vol. 269, No. 8, pp. 5833-5841.*
Nicholson, A.E. Predicting Stability of Lyophilized Products. (1976) Dev. Biol. Stand. vol. 36, pp. 69-75.*
Harrod, Kevin S., et al., "SP-A enhances viral clearance and inhibits inflammation after pulmonary adenoviral infection". *American Journal Physiology*, vol. 277, No. 3 part 1, L580-L588, 1999.
Hartshorn, Kevan L., et al., "Evidence for a Protective Role of Pulmonary Surfactant Protein D (SP-D) against Influenza A Viruses". *Journal of Clinical Investigation*, vol. 94, No. 1, 311-319, 1994.
LeVine, Ann Marie, et al., "Surfactant Protein-A-Deficient Mice Are Susceptible to *Pseudomonas aeruginosa* Infection". *American Journal of Respiratory Cell and Molecular Biology*, vol. 19, No. 4, 700-708, Oct. 1998.
Griese, M., "Pulmonary surfactant in health and human lung diseases: states of the art." *European Respiratory Journal*. 13:1455-1476, 1999.
LeVine, A.M. et al., "Surfactant Protein-A (SP-A) Binds Group B *Streptococcus* (GBS) Enhancing Phagocytosis and Clearance from Lungs of SP-A Deficient Mice." *J. Resp. Crit. Care Med.* vol. 157, A865, 1998.
Madan, T. et al. "Lung surfactant proteins A and D can inhibit specific IgE binding to the allergens of *Aspergillus fumigatus* and block allergen-induced histamine release from human basophils." *Clin. Exp. Immunol.* vol. 110, pp. 241-249, 1997.
King, R.J. "Pulmonary surfactant."*J. Appl. Physiol.: Respirat. Environ. Exercise Physiol.* vol. 53(1), pp. 1-8, 1982.
Wang, Jiu-Yao et al. "Inhibitory Effect of Pulmonary Surfactant Proteins A and D on Allergen-induced Lymphocyte Proliferation and Histamine Release in Children with Asthma." *Am. J. Respir. Crit. Care Med.* vol. 158, pp. 510-518, 1998.
King, R.J. et al. "Surfactant Protein-A Deficiency in a Primate Model of Bronchopulmonary Dysplasia" *Am. J. Respir. Crit. Care Med.* vol. 151, pp. 1989-1997, 1995.
LeVine, A.M. et al. "Surfactant Protein A-Deficient Mice are Susceptible to Group B Streptococcal Infection." *The Journal of Immunology*. vol. 158, pp. 4336-4340, 1997.
Thiel, S. et al., "Structures and Functions Associated with the group of mammalian lectins containing collagen-like sequences." *Federation of European Biochemical Societies*. vol. 250, No. 1, pp. 78-84, 1989.
Coalson, Jacqueline J. et al. "Pathophysiologic, Morphometric, and Biochemical Studies of the Premature Baboon with Bronchopulmonary Dysplasia." *Am. Rev. Respir. Dis.* vol. 145, pp. 872-881, 1992.
van Golde, L.M.G., ed., "Molecular Basis of Disease, Pulmonary surfactant." *Biochimica et Biophysica Acta*, 1408, pp. 77-78, 1998.

* cited by examiner

*Primary Examiner*—Nashaat T. Nashed
*Assistant Examiner*—Holly Schnizer
(74) *Attorney, Agent, or Firm*—Nath & Associates; Joshua B. Goldberg; Sheldon M. McGee

(57) ABSTRACT

Recombinant surfactant protein A and pharmaceutical compositions based thereon are useful for the prevention or treatment of pulmonary infection and inflammation.

20 Claims, 5 Drawing Sheets

RECOMBINANT SP-A FOR THE TREATMENT OR PREVENTION OF PULMONARY INFECTION AND INFLAMMATION

This application is a 371 of PCT/EP00/00324 filed Jan. 18, 2000, which claims the benefit of U.S. Provisional Patent Application Ser. No. 60/155,268, filed Jan. 19, 1999, now abandoned.

TECHNICAL FIELD

The present invention relates to the novel use of recombinant surfactant protein A for the production of a medicament for the treatment of pulmonary infection and inflammation.

PRIOR ART

Pulmonary surfactant plays an important role in maintaining the structural integrity of the alveoli by reducing surface tension. The surfactant consists mostly of a complex mixture of phospholipids and genetically distinct proteins referred to as surfactant protein A, B, C and D (also designated as SP-A, SP-B, SP-C and SP-D). It is synthesized by alveolar type II pneumocytes and secreted as tightly packed lamellar bodies into the alveoli (King, R. J.: Pulmonary Surfactant, J. Appl. Physiol. 1982, 51, 1–8).

SP-A is hypothesized to play a role in protecting the lung from bacterial, viral, and fungal infections (Thiel, S., and Reid, K.: Structures and functions associated with the group of mammalian lectins containing collagen-like sequences, FEBS Lett. 1989, 250, 78). In addition, in vitro, it has been shown that SP-A binds to various microorganisms, acts as opsonin, enhances killing of micro-organisms by macrophages, down regulates pro-inflammatory cytokines such as TNF-α induced by LPS or microbial pathogens (reviewed in: Molecular Basis of Disease, Pulmonary surfactant. Ed: L. M. G. van Golde, Biochimica et Biophysica Acta, 1998, 1408, 77–364).

Recently, it was shown that mice lacking SP-A are susceptible to group B streptococcal infection (LeVine A. M. et al.: Surfactant protein A-deficient mice are susceptible to group B streptococcal infection; The Journal of Immunology, 1997, 4336–4340) and that exogenous proteinosis SP-A enhanced bacterial clearance in SP-A deficient mice (LeVine A. M. et al.: Surfactant protein-A (SP-A) binds group B streptococcus (GBS), enhancing phagocytosis and clearance from lungs of SP-A deficient mice; Am J. Respir. Crit. Care Med. 1998, Vol. 157, A 865). In addition, it was shown that baboons with bronchopulmonary dysplasia (BPD) and superimposed infection have decreased levels of SP-A present in the lungs (King, R. J., et al.: Surfactant protein-A deficiency in a primate model of pulmonary dysplasia, Am. J. Respir. Crit. Care Med. 1995, 151(6), 1989–97 and Coalson, J. J.: Pathophysiologic, morphometric, and biochemical studies of the premature baboon with bronchopulmonary dysplasia, Am. Rev. Respir. Dis. 1992, 145, 872–81). Furthermore, it was shown that SP-A is decreased in a number of diseases such as pneumonia, asthma, bronchiolitis, lung transplantations, cystic fibrosis, ARDS, smokers etc. as reviewed in M. Griese, Pulmonary surfactant in health and human lung diseases: state of the art. Eur. Respir. J. 1999, 13, 1455–1476. It was also shown, that SP-A inhibits allergen induced histamine release as well as the proliferation of lymphocytes in cells isolated from allergen exposed asthmatics. (Wang, J. Y. et al., Inhibitory effect of pulmonary surfactant proteins A and D on allergen-induced lymphocyte proliferation and histamine release in children with asthma, Am. J. Respir. Crit. Care Med., 1998, 158, 510–518; Mandan, T. et al., Lung surfactants proteins A and D can inhibit specific IgE binding to the allergens of *Aspergillus fumigatus* and block allergen-induced histamine release from human basophills. Clin. Exp. Immunol., 1997, 110, 241–249).

SUMMARY OF THE INVENTION

The subject invention has several distinct aspects. One aspect is the use of a component which is at least substantially the same as recombinant surfactant protein A (rSP-A) for treating or preventing a pulmonary infection or inflammation. Another aspect is a medicament composition for treating or preventing a pulmonary infection and inflammation, and which comprises an active component which is at least substantially the same as recombinant surfactant protein A. A further aspect is a method of compounding such a medicament composition. A still further aspect comprises the concurrent use of surfactant protein D (SP-D) with an active component which is at least substantially the same as recombinant surfactant protein A in treating or preventing a pulmonary infection and inflammation, in compounding a medicament composition and in the resulting medicament composition itself. An additional aspect of the invention is an article of manufacture, comprising packaging material and rSP-A or a compound which is substantially the same as rSP-A (in a container) within the packaging material, and the packaging material including a label or instructions which indicate usefulness for the treatment or prevention of inflammation or microbial infection.

Details

Figure 1:
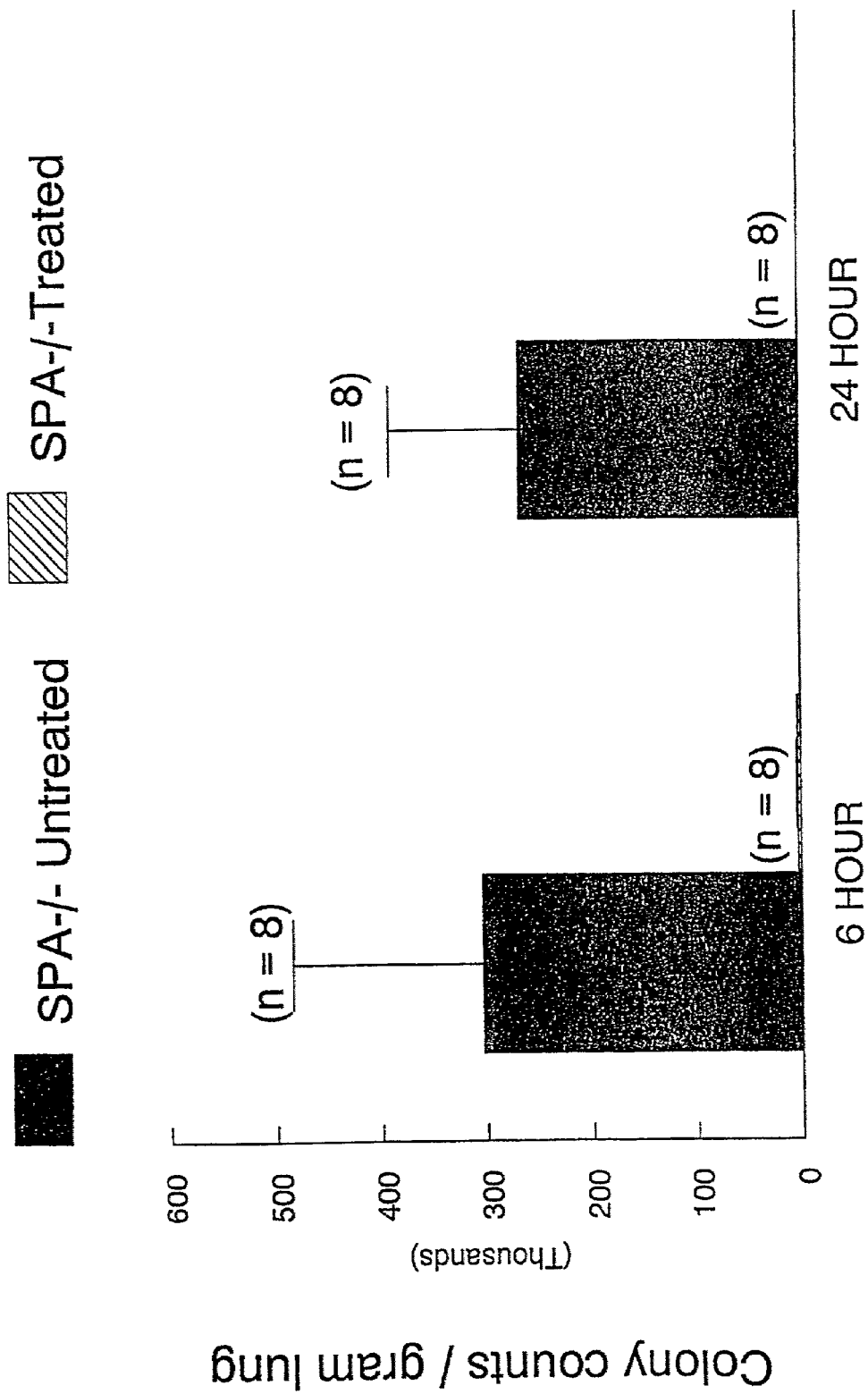
FIG. 1 graphically illustrates that the clearance of GBS in the SP-A (−/−) mice was significantly enhanced at 6 and 24 hours when GBS was co-administered with 150 μg rSP-A.

Surprisingly it has now been found that recombinant surfactant-associated protein A (rSP-A) can be used in the treatment or prevention of pulmonary infection and inflammation and is equivalent or superior to the use of surfactant-associated protein A (SP-A) obtained from natural sources, for example that isolated from lavage fluid from healthy individuals or proteinosis patients. This must be regarded as particularly surprising as SP-A isolated from human lung lavage consists of a homogenous population of a flower bouquet like hexameric structure, each unit of which consists of three SP-A polypeptide chains (α1), analogous to that described for the complement factor C1q. The fully assembled hexameric structure is thought to be essential for a functional molecule with respect to stimulating antimicrobial defense mechanisms or anti-inflammatory activity. In contrast to the naturally derived SP-A, surfactant-associated protein A produced by recombinant techniques consists of a variety of different oligomeric structures ranging from one single polypeptide chain (α1) to the fully assembled octadecameric form (γ6) (Voss, T., et al.: Macromolecular organization of natural and recombinant lung surfactant protein SP 28-36; J. Mol. Biol. 1988, 201, 219–227; Voss et al.: Structural comparison of recombinant pulmonary surfactant protein SP-A derived from two human coding sequences: Implications for the chain composition of natural human SP-A, Am. J. Respir. Cell Mol. Biol., 1991, 4, 88–94).

In addition it was shown, that natural derived SP-A is glycosylated. However, although recombinant produced SP-A, depending on the system used for expression (mammalian, insect, or yeast cells), shows different glycosylation patterns, it shows anti-microbial or anti-inflammatory effects superior or equivalent to the natural SP-A.

As used herein microbial refers to bacterial, viral or fungal.

As used herein recombinant surfactant-associated protein A (hereinafter also referred to as rSP-A) refers to vertebrate, preferably mammalian, surfactant-associated protein A produced by recombinant techniques. Amino acid sequences and DNA sequences coding for mammalian surfactant-associated protein A are, for example, described in WO86/03408, WO88/05820 and U.S. Pat. No. 4,882,422. Recombinant surfactant-associated protein A further refers to derivatives of vertebrate, preferably mammalian, surfactant-associated protein A produced by recombinant techniques which differ from natural mammalian or other vertebrate surfactant-associated protein A by addition, deletion or substitution of amino acids as long as the proteins retain microbial clearance activity or anti-inflammatory activity. Such activity of recombinant surfactant-associated protein A can, for example, be determined in an assay according to the one herein-after described for group B *streptococcus* bacteria. In a preferred embodiment rSP-A refers to human surfactant-associated protein A produced by recombinant methods and having an amino acid sequence encoded by a DNA sequence contained in cDNA clones, pHS10-5, pHS10-4, PSAP-1A, PSAP-6A and a genomic clone pHS-15 or an allelic variation thereof. Two genes (designated as A1 and A2) coding for SP-A have been identified in the human genome (White, R. T. et al.: Nature 1985, 317, 361–363; Katyal, S. L. et al.: Am. J. Respir. Cell Mol. Biol., 1992, 6:446–452). The genomic clone pHS-15 coding for human SP-A has been described in WO86/03408, and clones containing cDNA sequences coding for SP-A have been described in WO88/05820 for pHS10-5 and pHS10-4, and by Floros et al., The Journal of Biological Chemistry, 1986, 261, 9029–33 and U.S. Pat. No. 4,882,422 for PSAP-1A and PSAP-6A). Recombinant SP-A may be obtained according to procedures known in the art. Methods for cloning and production of rSP-A are for example described in WO86/03408, WO88/05820, U.S. Pat. No. 4,659,805, U.S. Pat. No. 4,912,038, Voss, T., et al.: Macromolecular organization of natural and recombinant lung surfactant protein SP 28-36; J. Mol. Biol. 1988, 201, 219–227, and Voss et al.: Structural comparison of recombinant pulmonary surfactant protein SP-A derived from two human coding sequences: Implications for the chain composition of natural human SP-A, Am. J. Respir. Cell Mol. Biol., 1991, 4 88–94).

In the text and drawings n refers to the number of animals (mice), and wt refers to "wild-type". As used in the claims, "substantially the same as" includes a) derivatives of surfactant-associated protein A produced by recombinant techniques, but which differ from natural surfactant-associated protein A by addition, deletion or substitution of one or more amino acids, b) SP-A modifications which differ in type and/or degree of glycosylation, and c) recombinant fusion proteins consisting of the complete or portions of the SP-A fused with suitable proteins or parts thereof having anti-infective or anti-inflammatory activities, as long as the surfactant-associated proteins A retain microbial clearance activity or anti-inflammatory activity, as determined by assay.

Examples which may be mentioned in connection with deleted, truncated or mutated forms of rSP-A are the SP-A-glob variant in which the amino acids of the collagenous domain were deleted (aa 17–80) or other forms as described in Spissinger et al., Assembly of the surfactant protein SP-A. Eur. J. Biochem., 1991, 199, 65–71.

Exemplary proteins having anti-infective or anti-inflammatory activities which may be mentioned in connection with recombinant fusion proteins are proteins such as defensins, lysozymes, cytokines, chemokines and immunoglobulins. These proteins can be fused to either the C- or N-terminal end of SP-A.

In one embodiment of the invention recombinant SP-A obtainable by expression of a DNA sequence coding for SP-A in a suitable eucaryotic expression system is used for the manufacture of a medicament for the prevention or treatment of pulmonary infection and inflammation. Suitable expression systems are, for example, CHO-cells using suitable expression vectors. Suitable expression vectors are, for example: pMT(E) Apo containing the SV40 enhancer and the inducible human metallothionin promoter (Fritz et al., Proc. Natl, Acad. Sci. USA, 83:4114–4118), pRc/CMV for constitutive expression of the gene of interest (Invitrogen, Leek, Netherlands) or any other expression vector useful for mammalian cells containing homologous intron sequences (i.e., authentic genomic sequences from the gene of interest) or heterologous intron sequences. In this case it is further preferred to use a partial or complete genomic sequence coding for SP-A, for example a genomic sequence as described in WO86/03408 for the A1 gene yielding a higher expression rate and subsequently to higher order structures of SP-A (Voss et at.: Structural comparison of recombinant pulmonary surfactant protein SP-A derived from two human coding sequences: Implications for the chain composition of natural human SP-A, Am. J. Respir. Cell Mol. Biol., 1991, 4:88–94). This approach would also apply for the A2 gene described by Katyal, S. L. et al. (Am. J. Respir. Cell Mol. Biol., 1992, 6:446–452). Preferentially the expression of the genomic sequence coding for SP-A in a suitable expression system is carried out as described by Voss et. al. (Am. J. Respir. Cell Mol. Biol. 1991, 4, 88–94).

In addition, to express the cDNA sequences coding for SP-A (A1/A2) it is preferred to use either insect cells using the Baculovirus expression system (McCormack, F. et al., J. Biol. Chem., 1994, 269:5833–5841) or yeast, such as *Pichia pastoris*, in both cases with or without co-expression of the human prolyl 4-hydroxylase stabilizing the collagen helices by hydroxylating proline residues in the collagenous domain as demonstrated for the expression of collagen (Lamberg, Arja et al., J. Biol. Chem., 1996, 271:11988–11995; Vuorela, A. et al., EMBO J., 1997, 16:6702–6712). For example rSP-A can be produced by cloning of the respective cDNAs into the EcoRI site of the Baculovirus expression vector pVL1392, subsequent generation of recombinant viruses and expression in SF21 cells using standard procedures. rSP-A may also be produced in yeast (for example *Pichia pastoris*) after cloning of the respective cDNAs into yeast expression vectors such as pPICZ A (Invitrogen, Leek, Netherlands) for the expression in *Pichia pastoris*.

In another embodiment of the invention recombinant SP-A obtainable by expression of a DNA sequence coding for SP-A in a suitable procaryotic expression system is used for the manufacture of a medicament for the prevention or treatment of pulmonary infection and inflammation.

In a further embodiment of the invention non-glycosylated rSP-A is used for the manufacture of a medicament for the prevention or treatment of pulmonary infection and inflammation.

A still further embodiment of the invention is an article of manufacture which comprises packaging material and a pharmaceutical agent within the packaging material wherein the pharmaceutical agent is at least substantially the same as rSP-A, and wherein the packaging material comprises a label or package insert which indicates that the pharmaceutical agent is useful for preventing or treating a pulmonary microbial infection or a pulmonary inflammation. The packaging material, label and package insert otherwise parallel or resemble what is generally regarded as standard packaging material, labels and package inserts for pharmaceuticals having related utilities.

Pharmacology

Methods

Animal Husbandry

The murine SP-A gene locus was targeted by homologous recombination as previously described (Korfnagen; T. R. et al.: "Altered surfactant function and structure in SP-A gene targeted mice; PNAS, 1996, 93, 9594–9599). Lungs of SP-A (−/−) mice do not contain detectable SP-A mRNA or protein. To limit variability related to strain differences, 129 J wild type (+/+) and SP-A (−/−) mice of the same strain were studied. Animals were housed and studied under IACUC-approved protocols in the animal facility of the Children's Hospital Research Foundation, Cincinnati. Male and female mice of approximately 20 to 25 grams (35 to 42 days old) were used. (LeVine A. M. et al.: Surfactant protein A-deficient mice are susceptible to group B streptococcal infection; The Journal of Immunology, 1997, 158, 4336–4340).

Recombinant SP-A

Recombinant SP-A was produced as described by Voss et al. (Am. J. Respir. Cell Mol. Biol. 1991, 4, 88–94).

Preparation of Bacteria

A stock culture of group B *streptococcus* (GBS) was obtained from a clinical isolate from a newborn with systemic infection. Bacteria were suspended in sterile phosphate-buffered saline (PBS) containing 20% glycerol and frozen in aliquots at −70° C. Bacteria from the same passage were used to minimize variations in virulence related to culture conditions. Before each experiment, an aliquot was thawed and plated on tryptic soy-5% defibrinated sheep blood agar then inoculated into 4 ml of Todd-Hewitt broth (Difco Laboratories, Detroit, Mich.) and grown for 14 to 16 hours at 37° C. with continuous shaking. The broth was centrifuged, and the bacteria were washed in PBS at pH 7.2 and resuspended in 4 ml of the buffer. In order to facilitate studies, a growth curve was generated so the bacterial concentration could be determined spectrophotometrically, which was confirmed by quantitative culture of the intratracheal inoculum.

Intratracheal Inoculation

Administration of GBS into the respiratory tract of the mice was performed by intratracheal inoculation of $10^4$ or $10^5$ cfu diluted in sterile normal saline (0.9% NaCl). To deliver GBS in the presence of rSP-A, GBS was diluted in 0.9% NaCl with 1 mM $Ca^{2+}$ and appropriate amounts of rSP-A in a 37° C. water bath for 30 minutes. Bacteria were delivered by intratracheal inoculation as previously described (LeVine A. M. et al.: Surfactant protein A-deficient mice are susceptible to group B streptococcal infection; The Journal of Immunology, 1997, 4336–4340).

Bacterial Clearance

Quantitative cultures of lung homogenates were performed 6 and 24 hours after inoculation of the animals with bacteria or bacteria together with SP-A, as previously described (LeVine A. M. et al.: Surfactant protein A-deficient mice are susceptible to group B streptococcal infection; The Journal of Immunology, 1997, 4336–4340). Bacterial clearance from the lungs of SP-A (−/−) mice was determined after intratracheal inoculation with GBS together with varying doses of rSP-A ranging from 25 μg, 50 μg, 75 μg, 100 μg to 150 μg. Wild-type animals were infected with GBS ($10^5$ cfu) and treated with rSP-A (150 μg) at the time of infection or 6 hours after infection.

Cytokine Production

Lung homogenates were centrifuged at 1,200×g and the supernatants were stored at −20° C. Tumor necrosis factor-α (TNF-α) levels were measured with ELISAs, using goat antimurine antibody (R&D Systems) directed against TNF-α. All plates were read on a microplate reader (Molecular Devices, Menlo Park, Calif.) and analyzed with the use of a computer-assisted analysis program (Softmax, Molecular Devices).

Statistical Methods

Since the distribution of the variable cfu/gram of lung was not normally distributed, a natural log transformation was used for all analyses. Analyses of variance (ANOVA) was performed to assess differences between the groups. Individual scores for each time point were compared using the median scores non parametric test. Findings were considered statistically significant at probability levels <0.05.

Results

Recombinant SP-A Increased Bacterial Clearance in SP-A (−/−) Mice

Figure 2:
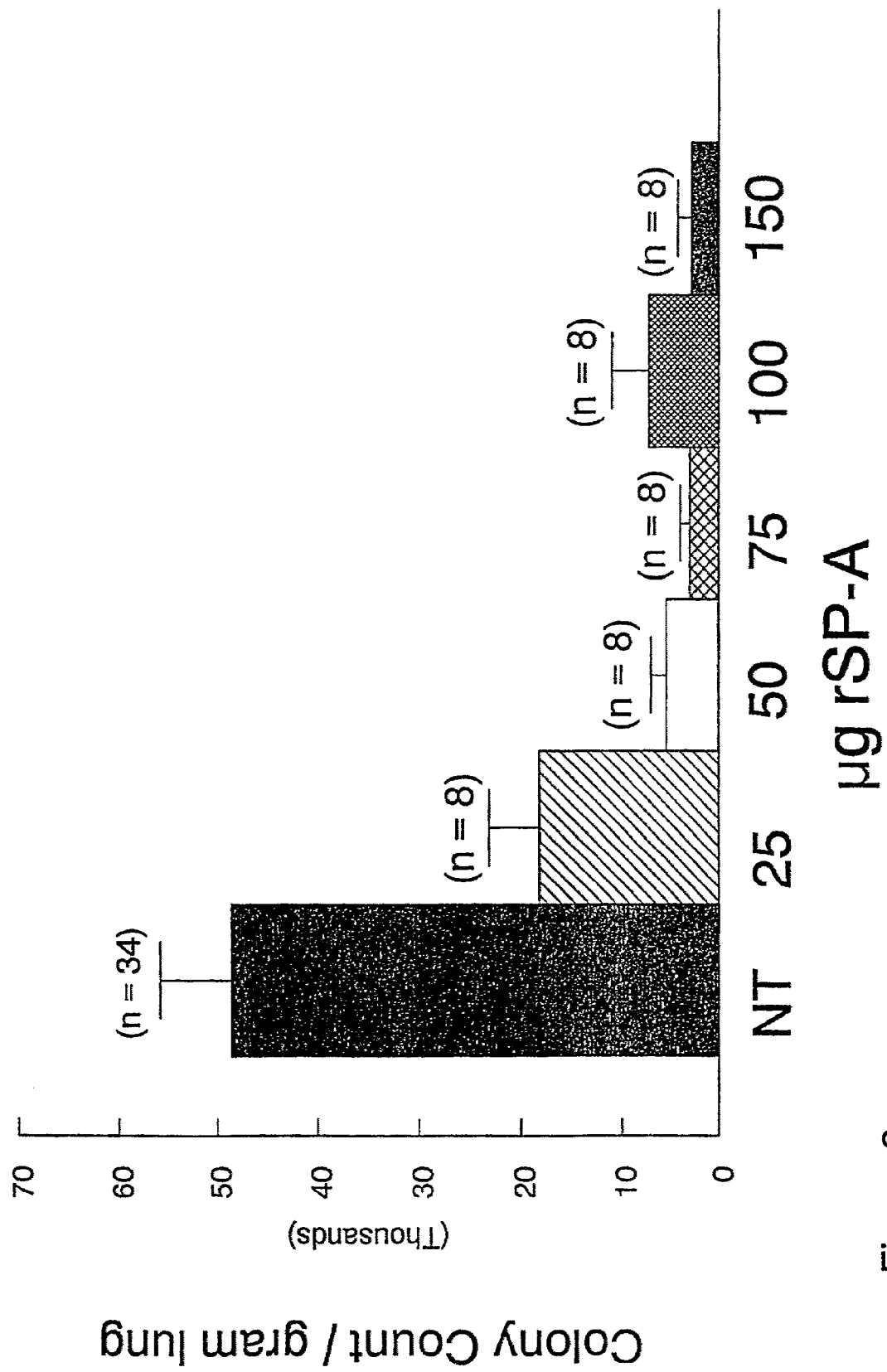
FIG. 2 graphically illustrates that GBS clearance by SP-A (−/−) mice is dose dependent and is increased by increased amount of rSP-A.

The clearance of GBS in the SP-A (−/−) mice was significantly enhanced at 6 and 24 hours when GBS was co-administered with 150 μg rSP-A (FIG. 1). Effects of rSP-A were comparable to that observed with SP-A isolated from proteinosis patients. GBS clearance by SP-A (−/−) mice was dose dependent and was increased by 50 μg, 75 μg, 100 μg and 150 μg of rSP-A (FIG. 2).

Recombinant SP-A Increased Bacterial Clearance in Wild-Type Mice

Figure 3:
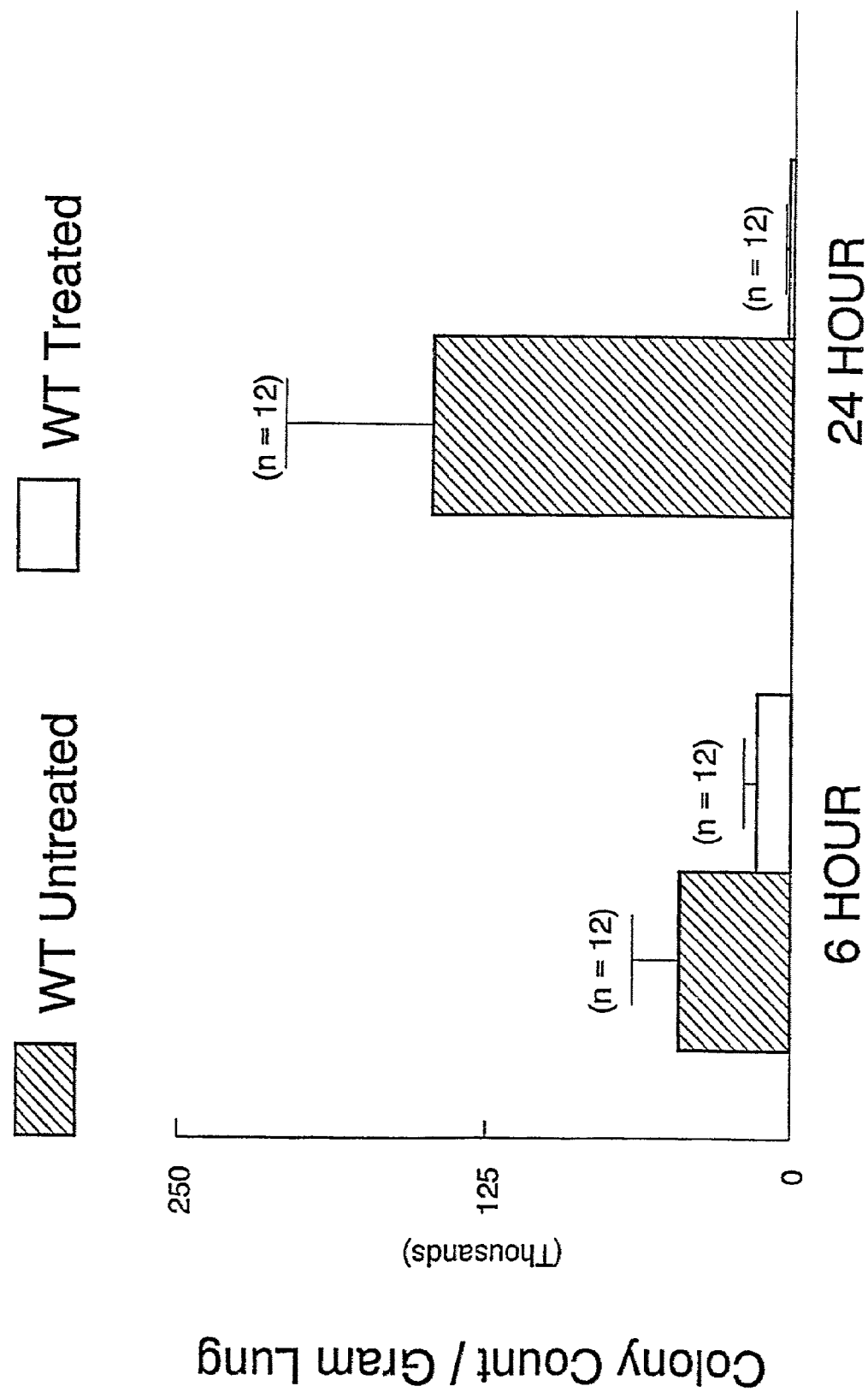
FIG. 3 graphically illustrates the clearance of GBS in wild-type mice is significantly enhanced at 6 and 24 hours when GBS is co-administered with 150 μg rSP-A.
Figure 4:
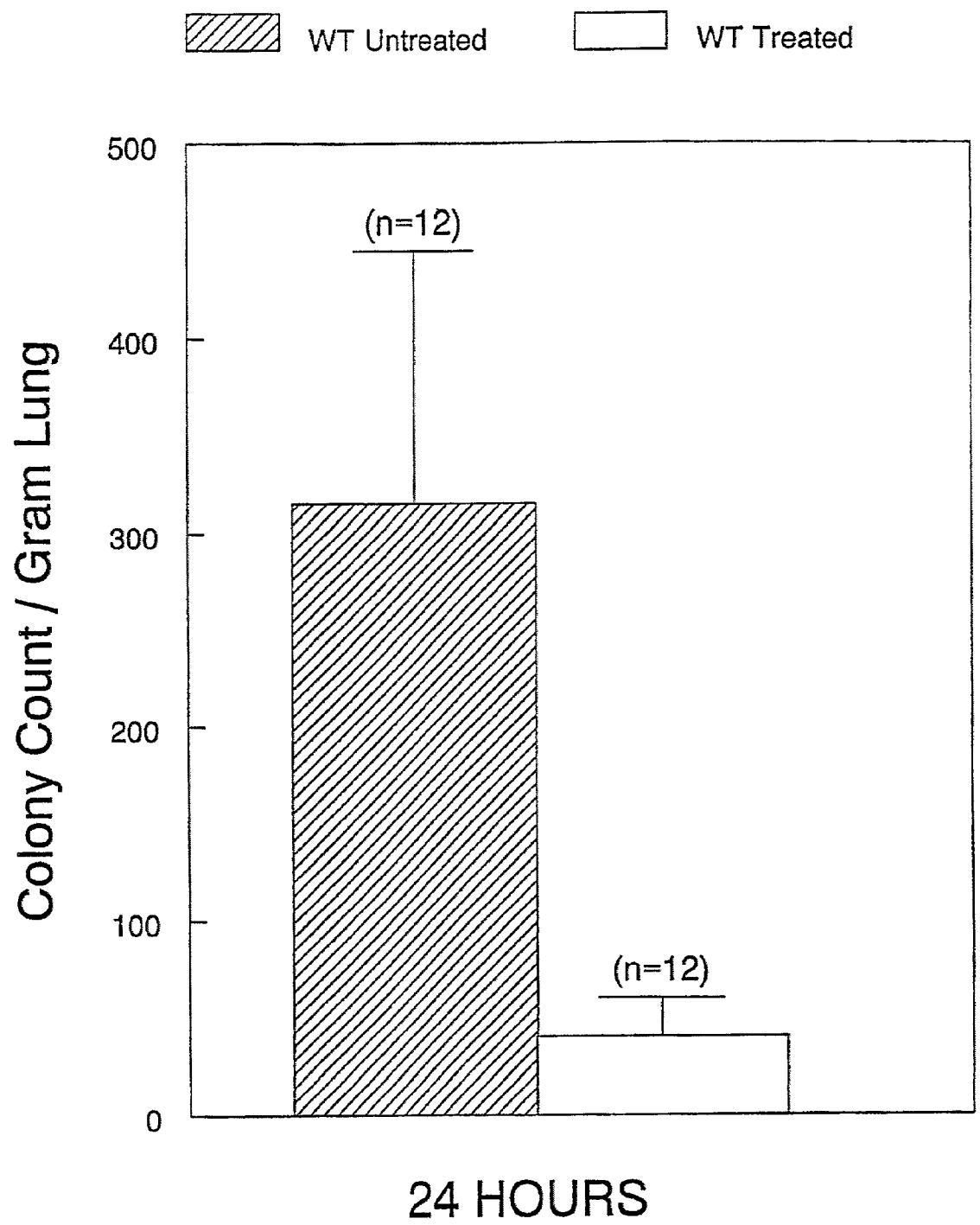
FIG. 4 graphically illustrates that wild-type animals infected with GBS and treated 6 hours after infection with intratracheal rSP-A have increased clearance of GBS at 24 hours.

The clearance of GBS in wild-type mice was significantly enhanced at 6 and 24 hours when GBS was co-administered with 150 μg rSP-A (FIG. 3). Wild-type animals infected with GBS and treated 6 hours after infection with intratracheal rSP-A (150 μg) had increased clearance of GBS at 24 hours (FIG. 4).

Pulmonary clearance of intratracheally administered GBS was reduced in SP-A (−/−) mice compared to wild-type mice. Co-administration of exogenous recombinant SP-A with the bacteria significantly improved bacterial clearance demonstrating an immediate reversible defect in the SP-A (−/−) mouse. Enhanced pulmonary clearance of GBS with rSP-A treatment was dose dependent. Wild-type mice were effectively treated with rSP-A with increased clearance of GBS from the lungs.

Figure 5:
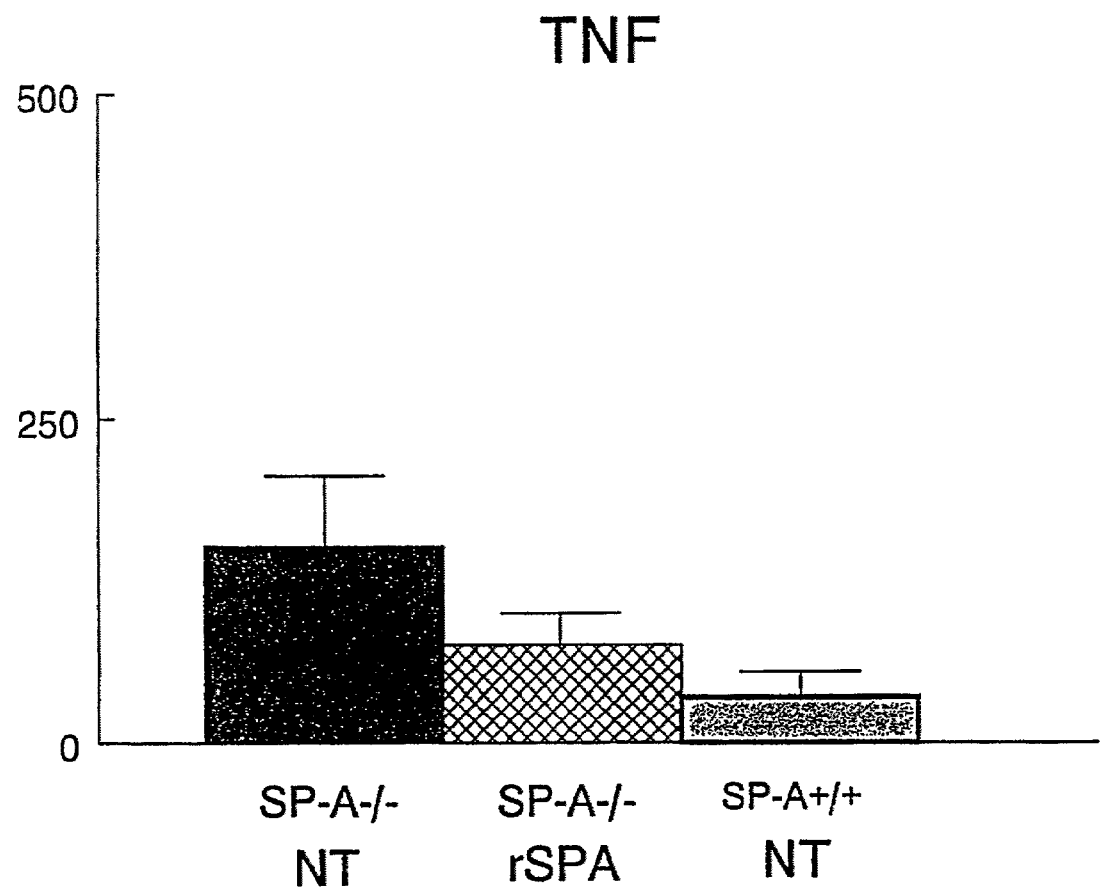
FIG. 5 graphically illustrates that exogenous rSP-A reduces TNF-α content in lung homogenates from SP-A (−/−) mice challenged with GBS close to the level observed in SP-A (+/+) mice.

In addition, it could be shown that exogenous rSP-A reduces TNF-α content in lung homogenates from SP-A (−/−) mice challenged with GBS close to the level observed in SP-A (+/+) mice (FIG. 5).

Utility

On account of its microbial clearance and anti-inflammatory properties rSP-A is useful for the manufacture of medicaments for the prevention or treatment of pulmonary infection and inflammation. As used herein pulmonary infection refers to microbial pneumonias caused, for example, by viruses like Respiratory Syncytial Virus, Adenovirus, Herpes simplex, Influenza A and others or bacteria like, *Pseudomonas aeruginosa, Staphylococcus aureus, Haemophilus influenzae, Kiebsiella pneumoniae*, Group B Streptococci, *Enterobacter* or *Streptococcus pneumoniae* and others, as well as fungi like *Aspergillus fumigatus, Pneumocystis carinii, Candida albicans* and others.

Furthermore pulmonary infection also refers to cases of reduced immunity for example the immunoparalytic phase occurring during sepsis and to immunodeficiency syndromes, whether congenital, spontaneously acquired, or iatrogenic. They are characterized by unusual susceptibility to infection and not infrequently to autoimmune disease and lymphoreticular malignancies. Patients with defects in humoral immunity have recurrent or chronic sinopulmonary infection, meningitis, and bacteremia, most commonly caused by pyogenic bacteria, such as *Haemophilus influenzae, Streptococcus pneumoniae*, and Staphylococci. These and other pyogenic organisms also cause frequent infections in individuals who have either neutropenia or a deficiency of the pivotal third component of complement (C3).

In connection with the present invention pulmonary inflammation refers, e.g., to bronchopulmonary dysplasia (BPD), and rSP-A therefore is also useful for the manufacture of medicaments for the prevention or treatment of bronchopulmonary dysplasia (BPD) or other disorders of SP-A deficiency. In particular BPD caused by artificial ventilation of premature babies may be mentioned in connection with the present invention. Additionally, inflammation also refers to pulmonary inflammation caused by artificial ventilation or cases of release of cytokines into the lung not primarily due to bacteria, viruses or fungi. Inflammation includes also diseases like asthma, CF (cystic fibrosis) and COPD (chronic obstructive pulmonary disease). It also includes acute lung injury up to the worst stages known as ARDS. In addition, inflammation also refers to inflammation induced by allergens.

The present invention also refers to the treatment of bacterial pulmonary infections with rSP-A or suitable forms thereof in combination or addition to antibiotics in the way that the infection induced inflammation is cured.

The invention furthermore relates to a method for the treatment of mammals, including humans, who are suffering from one of the above-mentioned illnesses. The method is characterized in that a therapeutically active and pharmacologically tolerable amount of rSP-A is administered to the mammal in need thereof.

In connection with the novel use of rSP-A according to the invention medicaments are prepared by procedures familiar to those skilled in the art. To do this rSP-A is either employed as such or preferably in combination with suitable pharmaceutical auxiliaries, e.g., as suspensions, solutions or in powder form, the rSP-A content advantageously being from 0.1 to 90% (wt/wt), preferably 0.1 to 15% (wt/wt). The rSP-A can be administered either alone or with auxiliaries. The auxiliaries which are suitable for the desired pharmaceutical formulations are familiar to the person skilled in the art on account of his expert knowledge. Pharmaceutical formulations which can be used according to the present invention and containing rSP-A in combination with synthetic or natural lipids are, for example, disclosed in U.S. Pat. No. 4,659,805. Surprisingly, and in contrast to pharmaceutical formulations comprising rSP-A disclosed in the state of the art, lipid free formulations comprising rSP-A as active ingredient can also be used for the treatment of pulmonary infection and inflammation. A further aspect the invention thus relates to lipid free medicaments comprising rSP-A.

In particular such lipid free medicaments comprising rSP-A contain as auxiliary from 0.01 to 0.1% of a calcium salt, preferably calcium chloride. An exemplary liquid, lipid free medicament can be manufactured by dissolving 100 to 1,000 mg of rSP-A and 11.1 mg of calcium chloride in 100 ml of a sterile 0.9% aqueous sodium chloride solution.

In a preferred embodiment the medicaments are made available in liquid form for intratracheal or intrabro n-chial administration by instillation or nebulization or in powder form for administration by inhalation.

In connection with the novel use of rSP-A according to the invention medicaments are administered, for example, 2 to 3 times daily for from 1 to 7 days. For example medicaments comprising 100 µg/kg to 10 mg/kg (of body weight) of rSP-A are administered by inhalation or intratracheally or intrabronchially.

In a further aspect of the invention rSP-A is administered in combination with surfactant proteins SP-B, SP-C and/or SP-D or their modified derivatives for the treatment or prevention of pulmonary infection and inflammation. In particular the co-administration of rSP-A with SP-D is preferred in connection with the invention. The amino acid sequences of said surfactant proteins, their isolation or preparation by genetic engineering are known (e.g. from WO86/03408, EP-A-0 251 449, WO89/04326, WO87/06943, WO88/03170, EP-A-0 368 823, EP-A-0 348 967, WO91/18015, WO95/32992, EP-A-0 593 094, WO92/22315 and Crouch et al.: Recombinant Pulmonary Surfactant Protein D, The Journal of Histological Chemistry, 1994, 269, 15808–15813 and references cited therein).

DESCRIPTION OF FIGURES

FIG. 1: Enhanced clearance of GBS from the lung in SP-A (−/−) mice, $10^4$ cfu GBS were inoculated with or without 150 µg of rSP-A, and colony counts were performed after 6 and 24 hours as previously de-scribed. SP-A (−/−) without rSP-A (solid bars) and with rSP-A (hatched bars). Data are Means±SEM (standard error of means) values.

FIG. 2: Enhanced clearance of GBS by exogenous rSP-A is dose dependent. SP-A (−/−) mice were inoculated with $10^4$ cfu GBS in the presence of either 0 (N.T.), 25, 50, 75, 100 or 150 µg of rSP-A, and colony counts were performed 6 hours after intratracheal instillation as previously described. Data are Means±SEM values.

FIG. 3: Enhanced clearance of GBS from the lung in SP-A (+/+) mice (wt). $10^6$ cfu GBS were inoculated with or without 150 µg of rSP-A and colony counts were performed 6 and 24 hours after intratracheal instillation as previously described. SP-A (+/+) without rSP-A (hatched bars) and with rSP-A (solid bars). Data are Means±SEM values.

FIG. 4: Rescue of GBS infection in SP-A(wt) mice. SP-A (+/+) mice were intratracheally inoculated with $10^6$ cfu GBS in the absence of exogenous rSP-A. 6 hours after infection, 150 µg of rSP-A were intratracheally administered. 24 hours after rSP-A administration colony counts in lungs were performed. Colony counts were dramatically reduced in lungs from animals treated with rSP-A (solid bars) compared to untreated animals (hatched bars). Data are Means±SEM values.

FIG. 5: rSP-A reduces TNF-α content in lung homogenates from SP-A (−/−) mice challenged with GBS. SP-A (−/−) and SP-A (+/+) mice were intratracheally inoculated with $10^4$ cfu GBS, in the absence or presence of exogenous 150 µg rSP-A. 6 hours after infection lungs were removed, homogenized, and the level of TNF-α was measured as previously described. SP-A (−/−) untreated (solid bar), SP-A (−/−) treated (cross hatched bar), SP-A (+/+) mice untreated (dotted bar). Data are expressed in pg/ml and represent means±SEM values with n=6 mice per group.

The invention and its advantages are readily understood from the preceding description. Various changes may be made in the processes and compositions without departing from the spirit and scope of the invention or sacrificing its material advantages, the processes and products hereinbefore described being merely illustrative of preferred embodiments of the invention.

What is claimed is:

1. A method for treating a pulmonary infection or inflammation in a patient prone to or afflicted with such condition, comprising administering to a patient in need thereof a therapeutically effective amount of a lipid-free pharmaceutical composition in powder form comprising a pharmaceutically acceptable active component and a suitable carrier therefor, wherein the active component comprises recombinant surfactant protein A (rSP-A).

2. A method for treating a pulmonary infection in a patient prone to or afflicted with such condition, comprising administering to a patient in need thereof a therapeutically effective amount of a lipid-free pharmaceutical composition in powder form comprising a pharmaceutically acceptable active component and a suitable carrier therefor, wherein the active component comprises recombinant surfactant protein A (rSP-A).

3. The method according to claim 2, wherein the pulmonary infection is bacterial, viral or fungal pneumonia.

4. A method for treating a pulmonary inflammation in a patient prone to or afflicted with such condition, comprising administering to a patient in need thereof a therapeutically effective amount of a lipid-free pharmaceutical composition in powder form comprising a pharmaceutically acceptable active component and a suitable carrier therefor, wherein the active component comprises recombinant surfactant protein A (rSP-A).

5. The method according to claim 4, wherein the pulmonary inflammation is bronchopulmonary dysplasia.

6. A method for treating a pulmonary infection or inflammation in a patient prone to or afflicted with such condition, comprising administering to a patient in need thereof a therapeutically effective amount of a lipid-free pharmaceutical composition comprising a pharmaceutically acceptable active component and a suitable carrier therefor, wherein the active component comprises recombinant surfactant protein A (rSP-A).

7. A method for treating a pulmonary infection in a patient prone to or afflicted with such condition, comprising administering to a patient in need thereof a therapeutically effective amount of a lipid-free pharmaceutical composition comprising a pharmaceutically acceptable active component and a suitable carrier therefor, wherein the active component comprises recombinant surfactant protein A (rSP-A).

8. The method according to claim 7, wherein the pulmonary infection is bacterial, viral or fungal pneumonia.

9. A method of treating a pulmonary infection or inflammation in a patient prone to or afflicted with such condition, comprising administering to a patient in need thereof a therapeutically effective amount of a lipid-free pharmaceutical composition in powder form comprising a pharmaceutically acceptable active component and a suitable carrier therefor, wherein the active component comprises recombinant surfactant protein A (rSP-A) and surfactant protein D (SP-D).

10. A method for treating a pulmonary inflammation in a patient prone to or afflicted with such condition, comprising administering to a patient in need thereof a therapeutically effective amount of a lipid-free pharmaceutical composition comprising a pharmaceutically acceptable active component and a suitable carrier therefor, wherein the active component comprises recombinant surfactant protein A (rSP-A).

11. The method according to claim 10, wherein the pulmonary inflammation is bronchopulmonary dysplasia.

12. A lipid-free pharmaceutical composition in powder form comprising a pharmaceutically acceptable active component and a suitable carrier therefor, wherein the active component comprises recombinant surfactant protein A (rSP-A) and surfactant protein D (SP-D).

13. A lipid-free pharmaceutical composition comprising a pharmaceutically acceptable active component and a suitable carrier therefor, wherein the active component comprises recombinant surfactant protein A (rSP-A) and further comprises surfactant protein D (SP-D).

14. A method for treating a pulmonary infection in a patient prone to or afflicted with such condition, comprising administering to a patient in need thereof a therapeutically effective amount of a pharmaceutical composition according to claim 13.

15. The method according to claim 14, wherein the pulmonary infection is bacterial, viral or fungal pneumonia.

16. A method for treating a pulmonary inflammation in a patient prone to or afflicted with such condition, comprising administering to a patient in need thereof a therapeutically effective amount of a pharmaceutical composition according to claim 13.

17. The method according to claim 16, wherein the pulmonary inflammation is bronchopulmonary dysplasia.

18. A method of treating a pulmonary infection or inflammation in a patient prone to or afflicted with such condition, comprising administering to a patient in need thereof a therapeutically effective amount of a pharmaceutical composition according to claim 13.

19. An article of manufacture comprising packaging material and the pharmaceutical composition according to claim 13 contained within the packaging material, wherein the packaging material comprises a label or package insert which indicates that the active component is useful for treating a pulmonary microbial infection or inflammation.

20. An article of manufacture comprising packaging material and a lipid-free pharmaceutical composition in powder form comprising a pharmaceutically acceptable active component and a suitable carrier therefor, wherein the active component comprises recombinant surfactant protein A (rSP-A) and surfactant protein D (SP-D) contained within the packaging material, wherein the packaging material comprises a label or package insert which indicates that the active component is useful for treating a pulmonary microbial infection or inflammation.

* * * * *